(12) United States Patent
Tanaka et al.

(10) Patent No.: US 8,530,208 B2
(45) Date of Patent: Sep. 10, 2013

(54) METHOD FOR PRODUCING PHOSPHOLIPID

(75) Inventors: Tatsushi Tanaka, Takasago (JP); Yugo Iwasaki, Nagoya (JP)

(73) Assignees: Kaneka Corporation, Osaka (JP); National University Corporation Nagoya University, Aichi (JP)

( * ) Notice: Subject to any disclaimer, the term of this patent is extended or adjusted under 35 U.S.C. 154(b) by 0 days.

(21) Appl. No.: 13/382,815

(22) PCT Filed: Jul. 5, 2010

(86) PCT No.: PCT/JP2010/061414
§ 371 (c)(1),
(2), (4) Date: Jan. 6, 2012

(87) PCT Pub. No.: WO2011/004794
PCT Pub. Date: Jan. 13, 2011

(65) Prior Publication Data
US 2012/0100580 A1   Apr. 26, 2012

(30) Foreign Application Priority Data
Jul. 6, 2009 (JP) .................................. 2009-160011

(51) Int. Cl.
*C12P 7/62* (2006.01)
(52) U.S. Cl.
USPC ......................................... 435/135; 435/134
(58) Field of Classification Search
None
See application file for complete search history.

(56) References Cited

FOREIGN PATENT DOCUMENTS

| | | |
|---|---|---|
| JP | 5-236974 A | 9/1993 |
| JP | 8-056683 A | 3/1996 |
| JP | 8-059678 A | 3/1996 |
| JP | 8-325192 A | 12/1996 |
| JP | 2007-129973 A | 5/2007 |
| JP | 2010-068799 A | 4/2010 |

OTHER PUBLICATIONS

Awano et al., "Production of docosahexaenoic acid bounded phospholipids via phospholipase $A_2$ mediated bioconversion," Fisheries Science 2006; 72; 909-911.
Tanaka et al., "Synthesis of Phospholipids Containing Polyunsaturated Fatty Acids by Phospholipase $A_2$ mediated Esterification with Food-compatible Reagents," Journal of Oleo Science 59, (7) 375-380 (2010).
International Search Report issued in International Application No. PCT/JP2010/061414.
Verified Translation of PCT Written Opinion of the International Searching Authority, date of mailing Aug. 17, 2010, International Patent Applcation No. PCT/JP2010/061414.

*Primary Examiner* — Nashaat Nashed
(74) *Attorney, Agent, or Firm* — Novak Druce Connolly Bove + Quigg LLP

(57) ABSTRACT

Provided is a method for producing a phospholipid at low cost by reusing phospholipase A2 in a method for producing the phospholipid whereby an arbitrary fatty acid is bonded to the 2-position of a phospholipid using an esterification reaction catalyzed by phospholipase A2 in glycerol. The method for producing a phospholipid is characterized by comprising conducting an esterification reaction catalyzed by phospholipase A2 between a lysophospholipid and an acyl donor in glycerol to from a phospholipid, adding a solvent immiscible with glycerol to form a glycerol layer and a solvent layer, extracting said phospholipid into said solvent layer, allowing phospholipase A2 to migrate into said glycerol layer, and, after separating the glycerol layer and distilling off the solvent remaining therein, further adding to the residual glycerol solution the lysophospholipid and the acyl donor to thereby conduct the esterification reaction again with use of phospholipase A2 remaining in said glycerol solution.

6 Claims, No Drawings

METHOD FOR PRODUCING PHOSPHOLIPID

CROSS REFERENCE TO RELATED APPLICATIONS

This application is a National Phase filing under 35 U.S.C. §371 of PCT/JP2010/061414, filed on Jul. 5, 2010; and this application claims priority to Application No. 2009-160011, filed in Japan on Jul. 6, 2009 under 35 U.S.C. §119; the entire contents of all are hereby incorporated by reference.

TECHNICAL FIELD

The present invention relates to methods for producing phospholipids, and in particular relates to methods for producing phospholipids by phospholipase A2.

BACKGROUND ART

Recent studies on lipids have revealed that highly unsaturated fatty acids such as docosahexaenoic acid (DHA) and eicosapentaenoic acid (EPA) have various functions such as the improvement of learning function, the prevention of arteriosclerosis, and the improvement function of lipid metabolism. In particular, it has been revealed that the intake of DHA in a form bonded to a phospholipid such as phosphatidylcholine provides higher antioxidant activity and higher stability than those of the triglyceride form as well as it leads to good absorption to readily provide physiological activities of the DHA. Functional fatty acids other than DHA, such as EPA, conjugated linoleic acid, and arachidonic acid are also expected to achieve higher physiological activities by the bonding to a phospholipid.

Methods for producing a phospholipid bonded with a functional fatty acid such as DHA are classified into a method of extraction of a natural product and a method of synthesis from a material such as soybean phospholipids. Specific examples of the former method include a method of extraction of a DHA-bonded phospholipid from aquatic animal roes as a material (Patent Document 1) and a method of extraction from marine products such as a squid with an organic solvent (Patent Document 2). However, these methods cannot produce phospholipids bonded with functional fatty acids other than DHA because the materials are expensive and cannot stably be supplied and the composition of phospholipid depends on materials.

Examples of methods capable of introducing a desired fatty acid not depending on a material composition include a method by adding any fatty acid to a culture solution of a microorganism to produce a phospholipid bonded with the fatty acid by the microorganism (Patent Document 3). However, the method produces the phospholipid in a small amount from a large amount of the culture solution and thus the production efficiency is poor.

Among the latter methods, examples of the method of bonding DHA to soybean phospholipids and the like include a method of adding a high-permittivity substance capable of forming hydrogen bonds to a reaction system of lipase and phospholipase (Patent Document 4). However, the method can achieve a high reaction rate in the reaction of a lysophospholipid and a fatty acid by the lipase but cannot achieve a high reaction rate by phospholipase A2. Furthermore, it is important for the expression of physiological activities of the DHA-bonded phospholipid that DHA is bonded to the 2-position, but a target fatty acid is mainly bonded to the 1-position in a phospholipid through a reaction by the lipase, and therefore such a method is not highly practical.

Meanwhile, as a method for efficiently bonding a desired fatty acid to the 2-position in a phospholipid, there have been reported some bonding methods using phospholipase A2 in glycerol (Patent Document 5 and Non-patent Document 1). However in these reports, toxic chloroform-methanol is used for extraction after the reaction. Thus, the solvent cannot be used depending on an intended use of the phospholipid, or an apparatus for removing the solvent is required. Moreover, the phospholipase A2 is expensive, and hence such a method is required to reduce costs.

In a common enzyme reaction, enzyme immobilization is widely performed for the efficient use of the enzyme. However, there have been reports that when an immobilized phospholipase A2 is used in esterification by the phospholipase A2, the esterification is unlikely to efficiently proceed even when a fatty acid is used in a large amount with respect to a lysophospholipid (Non-patent Document 2 and Non-patent Document 3).

CITATION LIST

Patent Literature
  Patent Document 1: JP-A No. 8-59678
  Patent Document 2: JP-A No. 8-325192
  Patent Document 3: JP-A No. 2007-129973
  Patent Document 4: JP-A No. 8-56683
  Patent Document 5: JP-A No. 5-236974
Non-Patent Literature
  Non-patent Document 1: Fisheries Science, Vol. 72, pages 909-911 (2006)
  Non-patent Document 2: Journal of the American Oil Chemists' Society, Vol. 72, pages 641-646 (1995)
  Non-patent Document 3: Biochimica et Biophysica Acta, Vol. 1343, pages 76-84 (1997)

SUMMARY OF INVENTION

Technical Problem

As described above, it is demanded to develop a method of recovering a phospholipid after efficient esterification by phospholipase A2 and of reusing the phospholipase A2. Hence, it is an object of the present invention to provide a method for producing a phospholipid at low cost by reusing phospholipase A2 in the method of producing the phospholipid bonded with any fatty acid to the 2-position in the phospholipid through esterification by the phospholipase A2 in glycerol.

Solution to Problem

The present inventors have carried out intensive studies in order to solve the problems, as a result, have found that, by esterifying a lysophospholipid by phospholipase A2 in glycerol, then extracting a phospholipid with a solvent immiscible with glycerol, then removing the solvent by evaporation, and adding the lysophospholipid and an acyl donor, re-esterification of the lysophospholipid with the acyl donor can be performed by reusing the phospholipase A2 remaining in glycerol, and the invention has been accomplished.

Namely, the present invention relates to a method for producing a phospholipid characterized by including producing a phospholipid through esterification of a lysophospholipid with an acyl donor by phospholipase A2 in glycerol, then adding a solvent immiscible with glycerol to form a glycerol layer and a solvent layer, extracting the phospholipid into the solvent layer, transferring the phospholipase A2 into the glycerol layer, then collecting the glycerol layer, removing a remaining solvent by evaporation from the glycerol layer to give a glycerol solution, adding the lysophospholipid and the acyl donor to the glycerol solution, and esterifying using the phospholipase A2 remaining in the glycerol solution.

In the present invention, a ketone solvent may be added as the solvent immiscible with glycerol, or an alcohol having 4 or less carbon atoms may be added after the esterification and then at least one solvent selected from the group consisting of hydrocarbon solvents, ketone solvents, and ester solvents may be added as the solvent immiscible with glycerol.

In the present invention, in the esterification, an amino acid and/or a peptide having three or less amino acid residues may be added to the reaction system.

The amino acid is preferably at least one selected from the group consisting of glycine, alanine, asparagine, glutamine, isoleucine, leucine, serine, threonine, valine, phenylalanine, and tyrosine.

The peptide is preferably a combination including glycine, alanine, and/or serine.

Advantageous Effects of Invention

According to the present invention, a method of producing a phospholipid at low cost by reusing phospholipase A2 in the method of producing the phospholipid bonded with any fatty acid to the 2-position in the phospholipid through esterification by the phospholipase A2 in glycerol can be provided.

Description of Embodiments

Hereinafter, the present invention will be described in further detail. The method for producing a phospholipid of the present invention is characterized by including producing a phospholipid through esterification of a lysophospholipid with an acyl donor by phospholipase A2 in glycerol then adding a solvent immiscible with glycerol to form a glycerol layer and a solvent layer, extracting the phospholipid into the solvent layer, transferring the phospholipase A2 into the glycerol layer, then collecting the glycerol layer, removing a remaining solvent by evaporation from the glycerol layer to give a glycerol solution, adding the lysophospholipid and the acyl donor to the glycerol solution, and re-esterifying using the phospholipase A2 remaining in the glycerol solution.

The lysophospholipid in the present invention is a compound of removing a fatty acid from the 2-position in a phospholipid and means a lipid different from phospholipids. The lysophospholipid used in the present invention may be a modified phospholipid and is preferably derived from soybeans, rapeseeds, and egg yolk due to easy availability. The lysophospholipid derived from soybeans is more preferred due to low cost, but lysophospholipids derived from other plants may be used.

Examples of the method for modifying a phospholipid to remove a fatty acid residue from the 2-position include, but are not necessarily limited to, a method of using phospholipase A2 or the like to hydrolyze the fatty acid residue at the 2-position in the phospholipid. The phospholipid usable in this case is a molecule having a skeleton, a phosphate group, and two fatty acid esters, is capable of being a substrate of the phospholipase A2, and does not include a molecule having a sphingosine skeleton. Specific examples include phosphatidylcholine, phosphatidylethanolamine, and phosphatidylserine. The method using the phospholipase A2 can be carried out without using any toxic substance, and therefore can be employed for the production of a phospholipid used, for example, for foods.

In the invention, the fatty acid as the acyl donor that is introduced to the 2-position of a lysophospholipid in the esterification of the lysophospholipid by phospholipase A2 in glycerol is not specifically limited. A free fatty acid may be used or an ethyl ester or a triglyceride is hydrolyzed by an enzyme such as lipase in a reaction system to be used, but from the viewpoint of reactivity, a free fatty acid is preferably used. Specific examples include, considering functionality, highly unsaturated fatty acids such as DHA, EPA, arachidonic acid, and conjugated linoleic acid. Examples of the usable DHA and EPA include free fatty acids that are obtained by hydrolysis of mainly marine animal oils or oils and fats derived from algae. The acyl donor used in the present invention is preferably used in an amount of 30 to 1000 parts by weight with respect to 100 parts by weight of a lysophospholipid from the viewpoints of reaction efficiency and costs.

When a fatty acid is difficult to be obtained as a single compound from natural resources, for example, DHA, a fatty acid mixture containing a desired fatty acid may be used. In such a case, the fatty acid mixture desirably includes a desired fatty acid in an amount of about 20% by weight or more. For example, in the case of DHA, a DHA-containing fatty acid mixture preferably has a DHA concentration of 20% by weight or more, and a mixture having a DHA concentration of 45% by weight or more is more preferably used. After the esterification according to the invention, solvent separation or the like may be carried out to increase the concentration of a phospholipid as the reaction product.

The phospholipase A2 used in the present invention may be derived from any source, and is preferably phospholipase A2 that can be commonly used for foods. Examples include those derived from porcine pancreas and microorganisms. The phospholipase A2 used in the present invention is preferably used in an amount of 1000 to 100000 U with respect to 1 g of a lysophospholipid from the viewpoints of reaction efficiency and costs.

In the present invention, the esterification is carried out in glycerol. This is because glycerol has high polarity to be effective for esterification and can be used for foods. It also has an advantage because it can dissolve amino acids described later as optional components. The glycerol is preferably used in an amount of 500 to 10000 parts by weight with respect to 100 parts by weight of a lysophospholipid, considering reactivity and the like.

In the present invention, the esterification is carried out in the glycerol as mentioned above, and hence, for the extraction of a resulted phospholipid, a solvent immiscible with the glycerol is used to extract the phospholipid. As the solvent immiscible with glycerol used in the present invention, at least one solvent selected from the group consisting of hydrocarbon solvents, ketone solvents, and ester solvents may be used, and the use of such a solvent leads to efficient extraction of a target phospholipid. Where, except for the extraction with the ketone solvent alone, it is preferable that an alcohol having 4 or less carbon atoms is added and then the solvent is added in order to reduce the viscosity of a reaction solution containing glycerol for easy extraction. The reason why the addition of the alcohol is not required when the ketone solvent is used alone is because it has higher solubility to glycerol than those of the hydrocarbon solvents and the ester solvents. The solvent is preferably added in an amount of 20 to 300 parts by weight with respect to 100 parts by weight of glycerol, considering recovery efficiency of a phospholipid and the like.

The hydrocarbon solvent means a compound capable of being used as a solvent among compounds composed of carbons and hydrogens alone. Specific examples include pentane, hexane, and heptane, and hexane is more preferred because it is readily removed by evaporation due to its low boiling point and can be used as a food additive.

The ketone solvent means a compound capable of being used as a solvent among compounds having a keto group in the molecule. Specific examples include acetone and butanone, and acetone is preferred because it is readily removed by evaporation due to its low boiling point and can be used as a food additive.

The ester solvent means a compound capable of being used as a solvent among compounds having an ester linkage in the molecule. Specific examples include methyl acetate and ethyl acetate, and ethyl acetate is preferred because it is used for foods.

In the present invention, in the esterification of a lysophospholipid by the phospholipase A2, an antioxidant may be used in order to suppress the oxidation of an acyl donor, and a calcium source such as calcium chloride, an amino acid, and a peptide having 3 or less amino acid residues may be used in order to activate the phospholipase A2. Other additives may also be used as necessary.

As the antioxidant, any antioxidant may be used as far as the antioxidative effect on fatty acids such as DHA can be expected, and examples include poly-phenols such as catechin, tocopherol, ascorbic acid, derivatives of them, and dibutylhydroxytoluene (BHT) from the viewpoint of food applications.

In order to suppress the oxidation of a fatty acid, the esterification of a lysophospholipid may be carried out under a nitrogen atmosphere without oxygen.

The amino acid means a compound mainly constituting a protein and having a carboxyl group and an amino group in the molecule, and is preferably a compound capable of being used for foods. Among them, neutral amino acids are preferred because such an amino acid can activate the phospholipase A2 while causing relatively little effect on a charge state of the phospholipase A2, and examples include glycine, alanine, asparagine, glutamine, isoleucine, leucine, serine, threonine, valine, phenylalanine, and tyrosine. For the method for producing a phospholipid of the present invention, at least one selected from them may be used.

The peptide having three or less amino acid residues means mainly a dimer or a trimer of amino acids through amide linkages. It may be synthesized from amino acids or may be a degradation product of a protein by an enzyme or the like. It is preferably a peptide including glycine, alanine, and/or serine because such a peptide has a comparatively high solubility to glycerol, and examples include glycylglycine. The use of such a peptide having a few amino acid residues leads to a high molarity when it is dissolved in glycerol and may efficiently activate the phospholipase A2.

The calcium source is used in order to activate the phospholipase A2 as described above and is preferably a compound capable of being present as a calcium ion in the reaction system. Thus, preferred calcium sources are compounds having a comparatively high solubility and also usable as food materials. Suitable examples of the calcium source include calcium chloride as mentioned above.

Each amount of the antioxidant, the calcium source, the amino acid, and the peptide having three or less amino acid residues may be an amount suitable for the achievement of each purpose. However, each of the amino acid and the peptide having three or less amino acid residues is preferably added in an amount of 10 to 2000 parts by weight with respect to 100 parts by weight of a lysophospholipid, and more preferably 50 to 500 parts by weight. The addition of such a compound in an amount of less than 10 parts by weight may reduce the reaction efficiency, and the addition of such a compound in an amount of more than 2000 parts by weight increases the cost and may reduce the reaction efficiency. Two or more of the amino acids and the peptides having three or less amino acid residues may be added in combination of them in order to increase the total dissolution amount in the esterification system.

A preferred example of the method for producing a phospholipid of the present invention be described below.

First, a lysophospholipid and an acyl donor are dissolved in glycerol; phospholipase A2 and, as necessary, an antioxidant and an amino acid, a peptide having three or less amino acid residues, and calcium chloride for activating the phospholipase A2 are added to give a glycerol reaction solution and the glycerol reaction solution is stirred to esterify the lysophospholipid with the acyl donor. As necessary, the esterification may be carried out under a nitrogen atmosphere without oxygen in order to suppress the oxidation of the fatty acid.

At this time, the esterification is preferably carried out at a temperature ranging from 35° C. to 80° C. and more preferably at a temperature ranging from 45° C. to 70° C. from the viewpoints of the optimum temperature of the phospholipase A2 and the suppression of the oxidation of the fatty acid as the acyl donor.

Depressurization may be carried out during the reaction in order to remove water that is formed through the esterification by the phospholipase A2 to accelerate the esterification. The depressurization for removing water may be carried out, for example, at a temperature of 35 to 80° C. at 150 torr (20 kPa) or less for 12 to 24 hours.

As described above, the esterification of the lysophospholipid with the fatty acid as the acyl donor forms a phospholipid introduced with the desired fatty acid to the 2-position of the lysophospholipid. The progress of the esterification may be checked by thin layer chromatography (TLC) and the like.

To the glycerol reaction solution containing the phospholipid formed through the esterification as above, a ketone solvent is added, or an alcohol having 4 or less carbon atoms is added to reduce the glycerol viscosity for easy extraction and then at least one solvent selected from the group consisting of hydrocarbon solvents, ketone solvents, and ester solvents is added to the reaction solution to form a glycerol layer and a solvent layer. Then, the phospholipid formed through the esterification is extracted into the solvent layer, the phosphpase A2 is transferred into the glycerol layer, and consequently the target phospholipid can be extracted. At this time, the solvent layer (upper layer) includes the target phospholipid/lysophospholipid, the solvent, and the acyl donor, and the glycerol layer (lower layer) mainly includes the glycerol, the solvent, the phospholipase A2, the phospholipid/lysophospholipid that cannot completely be extracted, other additives, and the like. Next, the solvent layer (upper layer) and the glycerol layer (lower layer) are separated (collected). At this time, the addition of a predetermined solvent and the separation may be properly repeated, considering the improvement of the phospholipid purity and the operating efficiency, In this manner, the target phospholipid can be efficiently extracted from the glycerol reaction solution.

The phospholipid and the phospholipase A2 can he separated as above, but the phospholipase A2 may be included in the solvent layer in a trace amount accompanying the target phospholipid. In this case, the target phospholipid may be mixed with the phospholipase A2 even after the treatment as exemplified below. Such a mixture including the phospholipase A2 may be used for foods, but, if necessary, the phospholipase A2 may be properly degraded and inactivated by, for example, using a degradative enzyme such as protease.

The alcohol having 4 or less carbon atoms means methanol, ethanol, propanol, and butanol, and ethanol is more preferred because it has low toxicity and can be used as a food additive. The alcohol is preferably added in an amount of 10 to 150 parts by weight with respect to 100 parts by weight of glycerol.

In the present invention, the fatty acid as the acyl donor may be removed from the separated solvent layer (upper layer) containing the target phospholipid as above. The method for removing the fatty acid as the acyl donor from the separated upper layer is not specifically limited, and examples of the method include a defatting method with a ketone solvent, an ethanol-hexane mixed solvent, or the like and a method of removing the fatty acid using silica gel.

For example, in the method using a ketone solvent or the like, the solvent in the separated (collected) upper layer is removed by evaporation; then a ketone solvent or the like is newly added; the mixture is cooled at 5° C. or less to precipitate the phospholipid; and the ketone solvent dissolving the fatty acid is separated and removed to give the phospholipid introduced with a desired fatty acid to the 2-position in the lysophospholipid. In the method, the ketone solvent or the like for adding after the solvent removal by evaporation is preferably acetone because it has a low boiling point to be readily removed by evaporation and can be used as a food additive.

In the method of removing the fatty acid using silica gel, the upper layer is separated (collected); then, the upper layer is passed through a column packed with silica gel to adsorb the phospholipid and to flow out the fatty acid for removal; then an eluent solvent such as methanol is passed through the column to desorb the phospholipid that is adsorbed to the silica gel and to collect a desired phospholipid fraction alone; then the phospholipid is recrystallized to give the phospholipid introduced with a desired fatty acid to the 2-position in the lysophospholipid.

Meanwhile, a solvent such as ethanol may inhibit the phospholipase A2 activity. Thus, the upper layer and the lower layer are separated (collected), and the glycerol layer as the lower layer may be decompressed to remove the remaining solvent. Such a treatment provides the glycerol solution containing the phospholipase A2, the remaining phospholipid/lysophospholipid, other optional additives, and the like.

Then, to the glycerol solution, the lysophospholipid as the reaction substrate and the fatty acid as the acyl donor are further added to achieve re-esterification using the phospholipase A2 remaining in the glycerol solution, and consequently the phospholipase A2 can be reused.

At this time, the manner of adding the lysophospholipid and the acyl donor is not specifically limited. To the glycerol solution, the lysophospholipid and the acyl donor may be simultaneously added, the lysophospholipid may be added followed by the addition of the acyl donor, or the acyl donor may be added followed by the addition of the lysophospholipid. Each amount may be properly adjusted so as to be substantially the same as that in the former esterification depending on the progress of the reaction or the extraction degree while considering that the unreacted lysophospholipid is present in the glycerol solution, Furthermore, the materials other than the lysophospholipid and the acyl donor, such as the calcium source, the amino acid and/or the peptide having three, or less amino acid residues, and the glycerol may be properly added in an amount reduced by the extraction of the phospholipid when the lysophospholipid and the acyl donor are added. The re-esterification may be carried out in the same conditions as those in the former esterification, and the extraction of the phospholipid may be carried out in the same manner as the above.

In this manner, as far as the phospholipase A2 maintains the activity, such an operation is repeated to reuse the phospholipase A2 many times, and consequently a desired phospholipid can be produced at lower cost. At this time, when the productivity of the phospholipid is lowered, the amount of the phospholipase A2, optional additives such as the amino acid, the peptide having three or less amino acid residues, and the calcium chloride, the glycerol, or the like may be partly reduced due to the extraction, or the activity of the phospholipase A2 or the like may be reduced. Hence, such a material may be added as necessary. Furthermore, in the same manner as in the former esterification, in order to suppress the oxidation of the fatty acid, the esterification may be carried out with an antioxidant or in a nitrogen atmosphere without oxygen, as necessary.

The method for producing a phospholipid of the present invention may be suitably employed as a method for producing a phospholipid introduced with a desired fatty acid to the 2-position. The method can be carried out without using materials and solvents such as chloroform unsuited for foods in the production process, and therefore is suitably employed especially for the production of edible phospholipids. Furthermore, the phospholipid obtained in this manner, in particular, the phospholipid introduced with a highly unsaturated fatty acid to the 2-position can be suitably used as a high-function edible phospholipid.

EXAMPLES

Hereinafter, the present invention will be described in further detail with reference to examples, but the present invention is not intended to be limited to the examples. In the examples, "part" and "%" are based on weight.

<Determination of Fatty Acid Composition in Phospholipid>

In Examples, Comparative Examples, and the like, after the completion of the reaction, to 50 µl of the reaction solution, 200 µl of a solvent of chloroform:methanol=2:1 (volume ratio) and 500 µl of a saturated sodium chloride solution were added, then the whole was stirred and centrifuged at 13000 rpm for 1 minute, and the lower layer was extracted. The centrifugation was carried out again using 200 µl of a solvent of chloroform:methanol=2:1 (volume ratio) in a similar manner, and the lower layer was extracted. The treated lower layer containing a phospholipid and a fatty acid was developed by TLC (thin layer chromatography) with the solvent to collect a fraction of the phospholipid and lysophospholipid. The fraction was esterified with sodium methylate to form methyl esters, and the fatty acid composition of the fatty acids bonded to the phospholipid and the lysophospholipid was analyzed with a gas chromatograph ("GC-14B" manufactured by Shimadzu Corporation). The area ratio % of each fatty acid in the gas chromatogram was regarded as the weight ratio % of the corresponding fatty acid.

Example 1

To 35 mg of lysophosphatidylcholine ("SLP-LPC70" manufactured by Tsuji Oil Mills Co., Ltd.), 105 mg of a DHA-containing fatty acid mixture that was prepared by common hydrolysis of DHA-50G (manufactured by Nippon Chemical Feed Co., Ltd., DHA content: 51.8% by weight) and 1 g of glycerol (manufactured by Sakamoto Yakuhin Kogyo Co., Ltd.) were added, and 37.5 mg of glycine (manufactured by Showa Denko K. K.) and. 37.5 mg of alanine (manufactured by Musashino Chemical Laboratory, Ltd.) were further added. Next, 20 mg of phospholipase A2 ("powdered Lysonase" manufactured by SANYO FINE CO., LTD., 53 U/mg) was further added, and the whole was decompressed at 0.6 torr (80 Pa) for 10 minutes to remove water.

Then, 10 µl of a 0.3 mol/l calcium chloride (manufactured by Tomita Pharmaceutical Co., Ltd.) solution and 30 µl of water were added, and the whole was reacted at 50° C. for 24 hours. The phospholipid and lysophospholipid fraction included in the reaction solution had a DHA content of 13.4% by weight.

To the reaction solution, 1 ml of ethanol vas added. The whole was stirred and then extracted with 1 ml of hexane twice to separate (collect) the hexane layer (upper layer) and the glycerol layer (lower layer) in a common procedure. As for the fatty acid composition of the phospholipid and lysophospholipid fraction included in each of the separated (collected) hexane layer (upper layer) and the glycerol layer (lower layer), the hexane layer had a DHA content of 20.7% by weight, and the layer had a DHA content of 6.3% by weight.

The separated (collected) glycerol layer (lower layer) was decompressed at 0.6 torr (80 Pa) for 15 minutes to remove the solvent. To the decompressed glycerol layer (glycerol solution), 18 mg of the lysophosphatidylcholine (SLP-LPC70) and 105 mg of the DHA-containing fatty acid mixture were added, then 40 µl of water was further added, and the whole was reacted at 50° C. for 24 hours. The phospholipid and lysophospholipid fraction included in the reaction solution had a DHA content of 13.6% by weight.

Example 2

To 35 mg of lysophosphatidylcholine ("SLP-LPC70" manufactured by Tsuji Oil Mills Co., Ltd.,), 30 mg of a DHA-containing fatty acid mixture that was prepared by common hydrolysis of Incromega DHA-J46 (manufactured by Croda Japan K.K., DHA content: 49.7% by weight) and 1 g of glycerol (manufactured by Sakamoto Yakuhin Kogyo Co., Ltd.) were added, and 25 mg of glycine (manufactured by Showa Denko K. K,) and 25 mg of alanine (manufactured by Musashino Chemical Laboratory, Ltd.) were further added. Next, 20 mg of phospholipase A2 ("powdered Lysonase" manufactured by SANYO FINE CO., LTD., 53 U/mg) was further added, and the whole was decompressed at 0.6 torr (80 Pa) for 10 minutes to remove water. Then, 10 µl of a 0.3 mol/l calcium chloride (manufactured by Tomita Pharmaceutical Co., Ltd.) solution was added, and the whole was reacted at 50° C. for 24 hours while decompressing at 50 torr (6.7 kPa). The phospholipid and lysophospholipid fraction included in the reaction solution had a DHA content of 16.9% by weight.

The reaction solution was extracted with 1 ml of acetone twice to separate (collect) the acetone layer (upper layer) and the glycerol layer (lower layer) in a common procedure. As for the fatty acid composition of the phospholipid and lysophospholipid fraction included in each of the separated (collected) acetone layer (upper layer) and the glycerol layer (lower layer), the acetone layer had a DHA content of 17.6% by weight, and the glycerol layer had a DHA content of 14.1% by weight.

The separated (collected) glycerol layer was decompressed at 0.6 torr (80 Pa) for 15 minutes to remove acetone. To the decompressed glycerol layer (glycerol solution), 30 mg of the lysophosphatidylcholine (SLP-LPC70) was added and stirred at 50° C. for 30 minutes to be dissolved, The DHA content in the phospholipid and lysophospholipid fraction included in the reaction solution was determined to be 4.8% by weight. To the mixture, 30 mg of the DHA-containing fatty acid mixture was added, and the whole was reacted at 50° C. for 24 hours while decompressing at 50 torr (6.7 kPa). The phospholipid and lysophospholipid fraction included in the reaction solution had a DHA content of 11.2% by weight after the reaction of 24 hours.

Example 3

To 50 mg of lysophosphatidylcholine (manufactured by Tsuji Oil Mills Co., Ltd. "SLP-WhiteLyso"), 30 mg of a DHA-containing fatty acid mixture that was prepared by common hydrolysis of Incromega DHA-J46 (manufactured by Croda Japan K.K., DHA content: 49.7% by weight) and 1 g of glycerol (manufactured by Sakamoto Yakuhin Kogyo Co., Ltd) were added, and 25 mg of glycine (manufactured by Showa Denko K. K.) and 25 mg of alanine (manufactured by Musashino Chemical Laboratory, Ltd.) were further added. Next, 20 mg of phospholipase A2 ("powdered Lysonase" manufactured by SANYO FINE CO., LTD., 53 U/mg) was further added, and the whole was decompressed at 0.6 torr (80 Pa) for 10 minutes to remove water. Then, 10 µl of a 0.3 mol/l calcium chloride (manufactured by Tomita Pharmaceutical Co., Ltd.) solution was added, and the whole was reacted at 50° C. for 24 hours white decompressing at 50 torr (6.7 kPa). The phospholipid and lysophospholipid fraction included in the reaction solution had a DHA content of 15.3% by weight.

To the reaction solution, 0.5 ml of ethanol was added. The whole was stirred and then extracted with a mixed solvent of 0.5 ml of hexane and 0.2 ml of acetone twice to separate (collect) the hexane/acetone layer (upper layer) and the glycerol layer (lower layer) in a common procedure. As for the fatty acid composition of the phospholipid and lysophospholipid fraction included in each of the separated (collected) hexane/acetone layer (upper layer) and the glycerol layer (lower layer), the hexane/acetone layer had a DHA content of 18.0% by weight, and the glycerol layer had a DHA content of 11.6% by weight.

The separated (collected) glycerol layer was decompressed at 0.6 torr (80 Pa) for 15 minutes to remove the solvent. To the decompressed layer (glycerol solution), 30 mg of the lysophosphatidyicholine (SLP-WhiteLyso) was added and stirred at 50° C. for 30 minutes to be dissolved. The DHA content in the phospholipid and lysophospholipid fraction included in the reaction solution was determined to be 6.6% by weight. To the mixture, 30 mg of the DHA-containing fatty acid mixture was added, and the whole was reacted at 50° C. for 24 hours while decompressing at 50 torr (6.7 kPa). The phospholipid and lysophospholipid fraction included in the reaction solution had a DHA content of 12.3% by weight after the reaction of 24 hours.

Example 4

To 50 mg of lysophosphatidylcholine (manufactured by Tsuji Oil Mills Co., Ltd. "SLP-WhiteLyso"), 30 mg of an EPA-containing fatty acid mixture that was prepared by common hydrolysis of EPA-45G (manufactured by Nippon Chemical Feed Co., Ltd., EPA content: 45.7% by weight) and 1 g of glycerol (manufactured by Sakamoto Yakuhin Kogyo Co., Ltd.) were added, and 25 mg of glycine (manufactured by Showa Denko K. K.) and 25 mg of alanine (manufactured by Musashino Chemical Laboratory, Ltd.) were further added. Next, 20 mg of phospholipase A2 ("powdered Lysonase" manufactured by SANYO FINE CO., LTD., 53 U/mg) was further added, and the whole was decompressed at 0.6 torr (80 Pa) for 10 minutes to remove water. Then, 10 µl of a 0.3 mol/l calcium chloride (manufactured by Tomita Pharmaceutical Co., Ltd.) solution was added, and the whole was reacted at 50° C. for 24 hours while decompressing at 50 torr (6.7 kPa). The phospholipid and lysophospholipid fraction included in the reaction solution had an EPA content of 19.5% by weight, To the reaction solution, 0.25 ml of ethanol was added. The whole was stirred and then extracted with 0.75 ml of ethyl acetate twice to separate (collect) the ethyl acetate layer (upper layer) and the glycerol layer (lower layer) in a common procedure. As for the fatty acid composition of the phospholipid and lysophospholipid fraction included in each of the separated (collected) ethyl acetate layer and the glycerol layer, the ethyl acetate layer had an EPA content of 22.1% by weight, and the glycerol layer had an EPA content of 17.8% by weight.

The separated (collected) glycerol layer was decompressed at 0.6 torr (80 Pa) for 15 minutes to remove the solvent. To the decompressed glycerol layer (glycerol solution), 36 mg of the lysophosphatidylcholine (SLP-WhiteLyso) was added and stirred at 50° C. for 30 minutes to be dissolved. The EPA content in the phospholipid and lysophospholipid fraction included in the reaction solution was determined to be 11.2% by weight. To the mixture, 30 mg of the EPA-containing fatty acid mixture was added, and the whole was reacted at 50° C. for 24 hours while decompressing at 50 torr (6.7 kPa). The phospholipid and lysophospholipid fraction included in the reaction solution had an EPA content of 16.3% by weight after the reaction of 24 hours.

Example 5

To 7.5 g of lysophosphatidylcholine (manufactured by Tsuji Oil Mills Co., Ltd, "SLP-WhiteLyso"), 3 g of a DHA-containing fatty acid mixture that was prepared by content: 49.7% by weight) and 100 g of glycerol (manufactured by Sakamoto Yakuhin Kogyo Co., Ltd) were added, and 3 g of glycine (manufactured by Showa Denko K. K.) and 3 g of alanine (manufactured by Musashino Chemical Laboratory, Ltd.) were further added. Next, 3 g of phospholipase A2 ("powdered Lysonase" manufactured by SANYO FINE CO., LTD., 53 U/mg) was further added, and 0.5 ml of a 2 mol/l calcium chloride (manufactured by Tomita Pharmaceutical Co., Ltd.) solution was added. The whole was reacted at 50° C. for 24 hours under a reduced pressure of 3 torr (0.40 kPa).

To the reaction solution, 50 ml of ethanol was added. The whole was stirred and then extracted with 50 ml of hexane twice to separate (collect) the hexane layer (upper layer) and the glycerol layer (lower layer) in a common procedure. The solvent in the separated hexane layer (upper layer) was removed by evaporation, and 50 ml of acetone was added. The whole was cooled at 0° C. for 1 hour to give 6.3 g of the target phospholipid as a precipitate. As for the fatty acid composition, the phospholipid had a DHA content of 17.0% by weight. As for the fatty acid composition of the phospholipid and lysophospholipid fraction, the separated glycerol layer (lower layer) had a DHA content of 8.3% by weight.

To the separated glycerol layer, 5.5 g of the lysophosphatidylcholine (SLP-WhiteLyso) and 3 g of the DHA-containing fatty acid mixture (prepared from Incromega DHA-J46) were added, The glycerol, layer was stirred at 100 torr (13 kPa) for 30 minutes to remove the solvent by evaporation, and reacted at 50° C. for 24 hours while decompressing at 3 torr (0.40 kPa), After the completion of the reaction, the reaction mixture was extracted with ethanol and hexane, and purified with acetone in a similar manner to the above to give 6.0 g of the target phospholipid. As for the fatty acid composition, the phospholipid had a DHA content of 15.8% by weight.

As described above, it was revealed that the reuse of phospholipase A2 can lead to the production of a phospholipid bonded with an arbitrary fatty acid to the 2-position of the phospholipid. Hereinafter, the results of the first esterification that used various amino acids, peptides having three or less amino acid residues, and the like will be described as Reference Examples.

As mentioned below, it is clear that the use of various amino acids, peptides having three or less amino acid residues, and the like can achieve an efficient production of a desired phospholipid. Therefore, the reuse of the phospholipase A2 with such a compound is also expected to achieve the efficient production of a desired phospholipid.

Reference Example 1

To 35 mg of lysophosphatidylcholine (manufactured by Tsuji Oil Mills Co., Ltd. "SLP-LPC70H"), 97 mg of oleic acid (manufactured by TOKYO CHEMICAL INDUSTRY CO., LTD.) and 1 g of glycerol (manufactured by Sakamoto Yakuhin Kogyo Co., Ltd.) were added, and 50 mg of glycine (manufactured by Wako Pure Chemical Industries, Ltd.) was further added. Next, 10 mg of phospholipase A2 ("Lecitase 100S" manufactured by Novozymes Japan, 130 U/mg) and 2.5 µl of a 1.0 mol/l calcium chloride (manufactured by Tomita Pharmaceutical Co., Ltd.) solution were further added, and the whole was reacted at 60° C. for 24 hours to give a phospholipid (phosphatidylcholine) bonded with oleic acid to the 2-position. As for the fatty acid composition, the obtained phospholipid and lysophospholipid fraction had an oleic acid content of 39.2% by weight.

Reference Example 2

To 35 mg of lysophosphatidylcholine ("SLP-LPC70" manufactured by Tsuji Oil Mills Co., Ltd.), 113 mg of DHA (manufactured by TOKYO CHEMICAL INDUSTRY CO., LTD.) and 1 g of glycerol (manufactured by Wako Pure Chemical Industries, Ltd.) were added, and 50 mg of glycine (manufactured by Wako Pure Chemical Industries, Ltd.) was further added. Next, 10 mg of phospholipase A2 ("Lecitase 100S" manufactured by Novozymes Japan, 130 U/mg) and 2.5 µl of a 1.0 Mol/l calcium chloride (manufactured by Wako Pure Chemical Industries, Ltd.) solution were added, and 3 mg of dibutylhydroxytoluene manufactured by Wako Pure Chemical Industries, Ltd.) was further added as an antioxidant. The whole was reacted at 60° C. for 48 hours to give a phospholipid (phosphatidylcholine) bonded with a highly unsaturated fatty acid (DHA) to the 2-position. As for the fatty acid composition, the obtained phospholipid and lysophospholipid fraction had a DHA content of 34.2% by weight.

Reference Example 3

To 35 mg of lysophosphatidylcholine (SLP-LPC70 manufactured by Tsuji Oil Mills Co., Ltd.), 113 mg of DHA (manufactured by TOKYO CHEMICAL INDUSTRY CO., LTD.) and 1 g of glycerol (manufactured by Wako Pure Chemical Industries, Ltd.) were added, and 60 mg of glycylglycine (manufactured by Wako Pure Chemical Industries, Ltd.) was further added. Next, 20 mg of phospholipase A2 (manufactured by SANYO FINE CO., LTD., powdered Lysonase, 53 U/mg) and 2.5 µl of a 1.2 mol/l calcium chloride (manufactured by Wako Pure Chemical Industries, Ltd.) solution were added, and 3 mg of Sankatol NO1 (manufactured by Tui Kagaku Co., Ltd.) containing catechin and 3 mg of ascorbic acid (manufactured by Wako Pure Chemical Industries, Ltd.) were further added as antioxidants. The whole was reacted at 60° C. for 48 hours to give a phospholipid (phosphatidylcholine) bonded with a highly unsaturated fatty acid (DHA) to the 2-position, As for the fatty acid composition, the obtained phospholipid and lysophospholipid fraction had a DHA content of 30.7% by weight.

Reference Example 4

A phospholipid bonded with a highly unsaturated fatty acid (EPA) to the 2-position was obtained in a similar manner to that in Reference Example 3 except that 104 mg of EPA (manufactured by NACALAI TESQUE, INC.) was used in place of 113 mg of DHA and 60 mg of glycine was used in place of 60 mg of glycylglycine. As for the fatty acid composition, the obtained phospholipid and lysophospholipid fraction had an EPA content of 28.5% by weight.

Reference Example 5

A phospholipid (phosphatidylcholine) bonded with a highly unsaturated fatty acid (arachidonic acid) to the 2-position was obtained in a similar manner to that in Reference Example 3 except that 103 mg of arachidonic acid (manufactured by Sigma-Aldrich Japan) was used in place of 113 mg of DHA and 40 mg of glycine was used in place of 60 mg of glycylglycine. As for the fatty acid composition, the obtained phospholipid and lysophospholipid fraction had an arachidonic acid .content of 32.3% by weight.

Reference Example 6

To 35 mg of lysophosphatidylcholine ("SLP-LPC70" manufactured by Tsuji Oil Mills Co., Ltd.), 105 mg of a DHA-containing fatty acid mixture that was prepared by common hydrolysis of DHA-50G (manufactured by Nippon Chemical Feed Co., Ltd., a DHA content of 51.8% by weight) and 1 g of glycerin (manufactured by Sakamoto Yakuhin Kogyo Co., Ltd.) were added, and 75 mg of glycine (manufactured by Showa Denko K. K.) was further added. Next, 20 mg of phospholipase A2 ("powdered Lysonase" manufactured by SANYO FINE CO., LTD.) was further added, and the whole was decompressed at 0.6 torr (80 Pa) for 10 minutes to remove water. Then, 10 μl of a 0.3 mol/l calcium chloride (manufactured by Tomita Pharmaceutical Co., Ltd.) solution was added, and the whole was reacted at 60° C. for 48 hours to give a phospholipid (phosphatidylcholine) bonded with a highly unsaturated fatty acid (DHA) to the 2-position. As for the fatty acid composition, the obtained phospholipid and lysophospholipid fraction had a DHA content of 15.5% by weight.

Reference Example 7

To 35 mg of lysophosphatidylcholine ("SLP-LPC70" manufactured by Tsuji Oil Mills Co., Ltd.), 105 mg of a DHA-containing fatty acid mixture that was prepared by common hydrolysis of DHA-50G (manufactured by Nippon Chemical Feed Co, Ltd., a DHA content of 51.8% by weight) and 1 g of glycerol (manufactured by Sakamoto Yakuhin Kogyo Co., Ltd,) were added, and 37.5 mg of glycine (manufactured by Showa Denko K. K.) and 37.5 mg of alanine (manufactured by Musashino Chemical Laboratory, Ltd.) were further added. Next, 20 mg of phospholipase A2 ("powdered Lysonase" manufactured by SANYO FINE CO., LTD.) was further added, and the whole was decompressed at 0.6 torr (80 Pa) for 10 minutes to remove water. Then, 10 μl of a 0.3 mol/l calcium chloride (manufactured by Tomita Pharmaceutical Co., Ltd.) solution was added, and the whole was reacted at 60° C. for 48 hours to give a phospholipid (phosphatidylcholine) bonded with a highly unsaturated fatty acid (DHA) to the 2-position. As for the fatty acid composition, the obtained phospholipid and lysophospholipid fraction had a DHA content of 17.2% by weight.

Reference Example 8

Preparation of Phospholipid-Containing Esterification Solution for Improving Purity of Phosphatidylcholine To 35 mg of lysophosphatidylcholine ("SLP-LPC70" manufactured by Tsuji Oil Mills Co., Ltd.), 30 mg of a DHA-containing fatty acid mixture that was prepared by common hydrolysis of DHA-50G (manufactured by Nippon Chemical Feed Co., Ltd., a DHA content of 51.8% by weight) and 1 g of glycerol (manufactured by Sakamoto Yakuhin Kogyo Co., Ltd.) were added, and 37.5 mg of glycine (manufactured by Showa Denko K. K.) and 37.5 mg of alanine (manufactured by Musashino Chemical Laboratory, Ltd.) were further added. Next, 20 mg of phospholipase A2 ("powdered Lysonase" manufactured by SANYO FINE CO., Ltd.) was added, and 6 μl of a 0.5 mol/l calcium chloride (manufactured by Tomita Pharmaceutical Co., Ltd.) solution was further added. The whole was decompressed at 0.6 torr (80 Pa) for 10 minutes to remove water, and reacted at 50° C. for 24 hours to give a phospholipid-containing esterification solution for improving the purity of a phosphatidylcholine. The phospholipid and lysophospholipid fraction included in the reaction solution had a DHA content of 15.3% by weight.

Comparative Example 1

A phospholipid bonded with oleic acid to the 2-position was obtained in a similar manner to that in Reference Example 1 except that glycine was not used. As for the fatty acid composition, the obtained phospholipid and lysophospholipid fraction had an oleic acid content of 19.4% by weight.

Comparative Example 2

A phospholipid bonded with a highly unsaturated fatty acid (DHA) to the 2-position was obtained in a similar manner to that in Reference Example 3 except that glycylglycine was not used. As for the fatty acid composition, the obtained phospholipid and lysophospholipid fraction had a DHA content of 12.9% by weight.

Comparative Example 3

A phospholipid bonded with a highly unsaturated fatty acid (EPA) to the 2-position was obtained in a similar manner to that in Reference Example 4 except that glycine was not used and 60 μl of water was added. As for the fatty acid composition, the obtained phospholipid and lysophospholipid fraction had an EPA content of 8.9% by weight.

Comparative Example 4

A phospholipid bonded with a highly unsaturated fatty acid (arachidonic acid) to the 2-position was obtained in a similar manner to that in Reference Example 5 except that glycine was not used. As for the fatty acid composition, the obtained phospholipid and lysophospholipid fraction had an arachidonic acid content of 5.5% by weight.

Comparative Example 5

A phospholipid bonded with a highly unsaturated fatty acid (DHA) to the 2-position was obtained in a similar manner to that in Reference Example 6 except that glycine was not used. As for the fatty acid composition, the obtained phospholipid and lysophospholipid fraction had a DHA content of 4.4% by weight.

Comparative Example 6

A phospholipid bonded with a highly unsaturated fatty acid (DHA) to the 2-position was obtained in a similar manner to that in Reference Example 8 except that glycine and alanine were not used. As for the fatty acid composition, the obtained phospholipid and lysophospholipid fraction had a DHA content of 7.6% by weight.

The invention claimed is:

1. A method for producing phospholipids, the method comprising:
   Incubating a reaction mixture comprising lysophospholipids, acyl donor, and phospholipase A2 in glycerol to produce phospholipids;
   adding a solvent immiscible with glycerol to form a glycerol layer and a solvent layer;
   extracting the phospholipid into the solvent layer;
   collecting the glycerol layer comprising the phospholipase A2;
   removing the remaining solvent by evaporation from the glycerol layer to give a glycerol solution;
   adding lysophospholipids and an acyl donor to the glycerol solution to form a reaction mixture; and incubate the reaction mixture to produce phospholipid.

2. The method for producing phospholipids according to claim 1, wherein a ketone solvent is added as the solvent immiscible with glycerol.

3. The method for producing phospholipids according to claim 1, wherein an alcohol having 4 or less carbon atoms is added after the production of phospholipids followed by the addition of at least one solvent immiscible with glycerol selected from the group consisting of hydrocarbons, ketones, and esters.

4. The method for producing phospholipids according to claim 1, wherein the reaction mixture comprises at least one amino acid and/or a peptide having three or less amino acid residues, wherein the at least one amino acid is selected from the group consisting of glycine, alanine, asparagine, glutamine, isoleucine, leucine, serine, threonine, valine, phenylalanine, and tyrosine, and wherein the peptide is a combination of amino acids including glycine, alanine, and/or serine.

5. The method for producing phospholipids according to claim 2, wherein the reaction mixture comprises at least an amino acid and/or a peptide having three or less amino acid residues is added to the esterification reaction system, wherein the at least one amino acid is selected from the group consisting of glycine, alanine, asparagine, glutamine, isoleucine, leucine, serine, threonine, valine, phenylalanine, and tyrosine, and wherein the peptide is a combination of amino acids including glycine, alanine, and/or serine.

6. The method for producing phospholipids according to claim 3, wherein the reaction mixture comprises at least one amino acid and/or a peptide having three or less amino acid residues is added, wherein the at least one amino acid is selected from the group consisting of glycine, alanine, asparagine, glutamine, isoleucine, leucine, serine, threonine, valine, phenylalanine, and tyrosine, and wherein the peptide is a combination of amino acids including glycine, alanine, and/or serine.

* * * * *